(12) United States Patent
Nakajima et al.

(10) Patent No.: US 11,672,920 B2
(45) Date of Patent: Jun. 13, 2023

(54) INTRADERMAL NEEDLE, PACKAGED ARTICLE, AND INJECTION DEVICE

(71) Applicant: TERUMO KABUSHIKI KAISHA, Tokyo (JP)

(72) Inventors: Kentaro Nakajima, Yamanashi (JP); Yoichiro Iwase, Kanagawa (JP)

(73) Assignee: TERUMO KABISHIKI KAISHA, Tokyo (JP)

( * ) Notice: Subject to any disclaimer, the term of this patent is extended or adjusted under 35 U.S.C. 154(b) by 317 days.

(21) Appl. No.: 16/815,301

(22) Filed: Mar. 11, 2020

(65) Prior Publication Data

US 2020/0206433 A1 Jul. 2, 2020

Related U.S. Application Data

(63) Continuation of application No. PCT/JP2019/008668, filed on Mar. 5, 2019.

(30) Foreign Application Priority Data

Mar. 16, 2018 (JP) .............................. JP2018-049360

(51) Int. Cl.
*A61M 5/32* (2006.01)
*A61M 5/00* (2006.01)

(52) U.S. Cl.
CPC .......... *A61M 5/3221* (2013.01); *A61M 5/002* (2013.01); *A61M 5/3202* (2013.01);
(Continued)

(58) Field of Classification Search
CPC ... A61M 5/002; A61M 5/3202; A61M 5/3216
See application file for complete search history.

(56) References Cited

U.S. PATENT DOCUMENTS 3,036,700 A * 5/1962 Krug ................... A61M 5/3202
206/469
4,747,836 A * 5/1988 Luther ................ A61M 5/3216
604/263
(Continued)

FOREIGN PATENT DOCUMENTS

CN 1520319 A 8/2004
CN 103269740 A * 8/2013 .......... A61M 5/3202
(Continued)

OTHER PUBLICATIONS

Translation WO2016158143A1 (Year: 2016).*
(Continued)

*Primary Examiner* — Laura A Bouchelle
(74) *Attorney, Agent, or Firm* — Buchanan Ingersoll & Rooney PC

(57) ABSTRACT

Provided are an intradermal needle having a protector that is movable from an open position near a needle hub to a closed position where a needle tip is covered, a packaged article, and an injection device. The protector has an arm that is supported in a freely pivotable manner by an axle pin positioned on the base end side of the wide diameter part of the intradermal needle, and a lid supported by the arm. With the axle of pivoting of the protector positioned near the needle hub, the lid may be housed compactly near the needle hub when the protector is in the open position.

24 Claims, 10 Drawing Sheets

(52) U.S. Cl.
CPC ........ *A61M 5/3216* (2013.01); *A61M 5/3293* (2013.01); *A61M 2005/3226* (2013.01)

(56) References Cited

U.S. PATENT DOCUMENTS

| | | | |
|---|---|---|---|
| 5,733,265 A * | 3/1998 | Bachman | A61M 5/3216 604/263 |
| 5,919,165 A | 7/1999 | Benson | |
| 6,298,541 B1 * | 10/2001 | Newby | A61B 5/150496 604/110 |
| 6,413,243 B1 | 7/2002 | Geist | |
| 2002/0156424 A1 | 10/2002 | Suzuki et al. | |
| 2005/0004531 A1 | 1/2005 | Hwang et al. | |
| 2015/0273159 A1 | 10/2015 | Zhang | |
| 2015/0335828 A1 | 11/2015 | Mathiasson | |
| 2016/0074598 A1 * | 3/2016 | Wang | A61M 5/3216 604/192 |
| 2016/0220766 A1 | 8/2016 | Kawano et al. | |
| 2016/0271337 A1 * | 9/2016 | Bubenik | A61M 5/3216 |
| 2017/0197035 A1 * | 7/2017 | Iwase | A61M 5/346 |
| 2020/0206432 A1 | 7/2020 | Nakajima et al. | |
| 2020/0206434 A1 | 7/2020 | Nakajima et al. | |

FOREIGN PATENT DOCUMENTS

| | | |
|---|---|---|
| CN | 103405831 A | 11/2013 |
| JP | 2015525605 A | 9/2015 |
| WO | 2016/020662 A1 | 2/2016 |
| WO | 2016158143 A1 | 10/2016 |
| WO | 2016158144 A1 | 10/2016 |
| WO | WO-2016158143 A1 * | 10/2016 ........ A61M 5/31515 |
| WO | 2017/001925 A1 | 1/2017 |

OTHER PUBLICATIONS

Translation CN 103269740A (Year: 2013).*
The extended European Search Report dated Jul. 31, 2020, by the European Patent Office in corresponding European Patent Application No. 19768652.0-1122. (8 pages).
U.S. Appl. No. 16/815,576, filed Mar. 11, 2020 entitled "Intradermal Needle, Packaging Article Thereof, and Injection Device", published as U.S. Application Publication No. 2020-0206432.
U.S. Appl. No. 16/815,794, filed Mar. 11, 2020 entitled "Intradermal Needle, Packaged Article Thereof, and Injection Device", published as U.S. Application Publication No. 2020-0206434.
International Search Report (PCT/ISA/210) dated May 28, 2019, by the Japanese Patent Office as the International Searching Authority for International Application No. PCT/JP2019/008668.
Written Opinion (PCT/ISA/237) dated May 28, 2019, by the Japanese Patent Office as the International Searching Authority for International Application No. PCT/JP2019/008668.
Office Action (The First Office Action) dated Mar. 10, 2022, by the State Intellectual Property Office of People's Republic of China in corresponding Chinese Patent Application No. 201980003861.6 and an English Translation of the Office Action. (18 pages).

* cited by examiner

INTRADERMAL NEEDLE, PACKAGED ARTICLE, AND INJECTION DEVICE

CROSS-REFERENCES TO RELATED APPLICATIONS

This application is a continuation of International Application No. PCT/JP2019/008668 filed on Mar. 5, 2019, which claims priority to Japanese Application No. 2018-049360 filed on Mar. 16, 2018, the entire content of both of which is incorporated herein by reference.

FIELD OF THE INVENTION

This invention generally relates to an intradermal needle used for injecting drug into living body, a packaged article, and an injection device.

BACKGROUND DISCUSSION

An intradermal needle has been proposed for injecting drug into an upper layer of skin. Since the intradermal needle is designed to keep a needle tip of a needle tube within the upper layer of skin, the needle tube has a length of protrusion of 3 mm or shorter. By virtue of such short length of protrusion of the needle tube, the intradermal needle is less likely to cause erroneous puncture, as compared with widely-used needles for hypodermic injection. Even in the case of the intradermal needle however, the needle tip remains exposed, so that there remains a risk that the needle tip of the needle tube may accidentally puncture the user after the drug administration or upon disposal of the injection device.

To address this problem, International Patent Application Publication No. 2016/158143 describes a technique of providing a pivotable protector to the intradermal needle. With the intradermal needle described in International Patent Application Publication No. 2016/158143, the needle tip can be prevented from accidentally puncturing the user, by pivoting the protector to cover the needle tip of the needle tube after use.

SUMMARY

No special attention has been paid, however, to the aforementioned intradermal needle in terms of convenience of housing in a packaged article, making the intradermal needle inconvenient to handle.

The intradermal needle disclosed here may be housed more conveniently into a packaged article, may be improved to be easier to handle, a packaged article, and an injection device.

According to one aspect of the disclosure, an intradermal needle comprises a tubular tube having a needle tip configured to puncture a living body, a needle hub supporting the tubular needle and possessing a central axis extending through the needle hub, with the needle hub including a front end side and a base end side on opposite axial sides of the needle hub, and a flange fixed to and extending outwardly from the needle hub so that the flange is an enlarged diameter part of the needle hub. The tubular needle projects away from the needle hub on the front end side of the flange, and a pivotable protector is pivotable about a pivot axis perpendicular to the central axis of the needle hub to pivot from an open position in which the needle tip is exposed and uncovered by the protector to a closed position in which the needle tip is covered by the protector. The protector is pivotably mounted on an axle part positioned on the base end side of the flange so that the protector pivots on the axle part about the pivot axis.

According to the aforementioned intradermal needle, the pivoting axle part of the protector may be positioned so as not to overlap the wide diameter part which is the widest part of the intradermal needle, so that the protector may be sized compactly. Hence, the intradermal needle with the protector may now be housed within a small packaged article having an inner diameter comparable to the diameter of the wide diameter part.

In the intradermal needle, the axle of pivoting of the pivoting axle part may be arranged near the axis of the needle hub. With such structure, the protector can pivot nearly centered round the needle hub, making it possible to compactly house the lid, in the open position, more closely to the axis of the needle hub.

In the intradermal needle, the protector may have an arm that extends from the pivoting axle part, and a lid supported by the arm, wherein each of the pivoting axle part and the arm may be provided as a pair while the needle hub is located between, and the lid may be supported by the pair of arms. With the lid thus supported by the pair of arms, the protector will have enhanced strength, and may be pivoted reliably around the axle of pivoting, even under force applied from directions other than the direction of pivoting, while preventing the arms and the lid from deforming.

In the intradermal needle, the wide diameter part may have formed therein a cutout side that extends in the direction of pivoting of the arms. With such structure, the wide diameter part is prevented from coming into contact with the arms in pivoting motion. Again in the intradermal needle, an interval or distance between the one arm and the other arm may be smaller than a diameter of the wide diameter part. This makes it possible to reduce the distance between the arms comparable to the width of the cutout side of the wide diameter part, to thereby downsize the protector, and to improve convenience for housing into the packaged article.

The intradermal needle may be provided with a restriction member that restricts pivoting of the protector in the open position and the closed position. This successfully prevents the lid of the protector from moving out of a predetermined range of pivoting, and from undesirably obstructing use of the intradermal needle.

In the intradermal needle, the pivoting axle part may have formed therein a resisting member that produces resistive force against pivoting of the protector. This successfully prevents the protector from unintentionally pivoting to obstruct use of the intradermal needle.

The intradermal needle may be provided with a lock mechanism that fixes the protector in the closed position. With this structure, the needle tip is prevented from being exposed, due to re-opening of the protector having been held in the closed position.

In the intradermal needle, the pivoting axle part may be arranged on a bracket mounted on the needle hub. This enables arrangement of the pivoting axle part near the needle hub, with a simple structure.

In the intradermal needle, a socket may be mounted so as to cover the wide diameter part from the base end side, and the pivoting axle part may be arranged on the socket. Further, the socket may have formed thereon a sliding face over which the protector slides, and the sliding face may be provided with a non-return mechanism that blocks reverse pivoting of the protector towards the open position. Further in the intradermal needle, the protector may be provided with a cutout formed by cutting out a part that falls, in the open position, within a predetermined range around the needle hub. With such socket mounted thereon, the strength will be enhanced since the arms of the protector are supported by the sliding face of the socket. In addition, the non-return mechanism can allow the protector to reliably pivot to the closed position.

According to another aspect of the disclosure, a packaged article of the intradermal needle includes the aforementioned intradermal needle, and a container that houses the intradermal needle, wherein the container has a bottom face configured so that the inner diameter of the container nearly equals the diameter of the wide diameter part of the intradermal needle, and the intradermal needle is housed in the container, with the protector in the open position. As described above, the intradermal needle has a protector that can be housed compactly, and the packaged article that houses them may use a container designed for intradermal needle having no protector.

According to still another aspect of the disclosure involves an injection device having the aforementioned intradermal needle, and a syringe attached to the intradermal needle in a detachable manner. Hence, after use of the injection device, the protector of the intradermal needle may be pivoted to the closed position to cover the needle tip, so that the intradermal needle may be disposed safely, without inducing erroneous puncture.

With the intradermal needle, the packaged article, and the injection device according to these aspects, convenience for housing in a small packaged article and convenience for handling will be improved.

DETAILED DESCRIPTION

Set forth below with reference to the accompanying drawings is a detailed description of embodiments of an intradermal needle, a packaged article that includes an intradermal needle, and an injection device representing examples of the inventive intradermal needle, packaged article and injection device disclosed here.

First Embodiment

Figure 1:
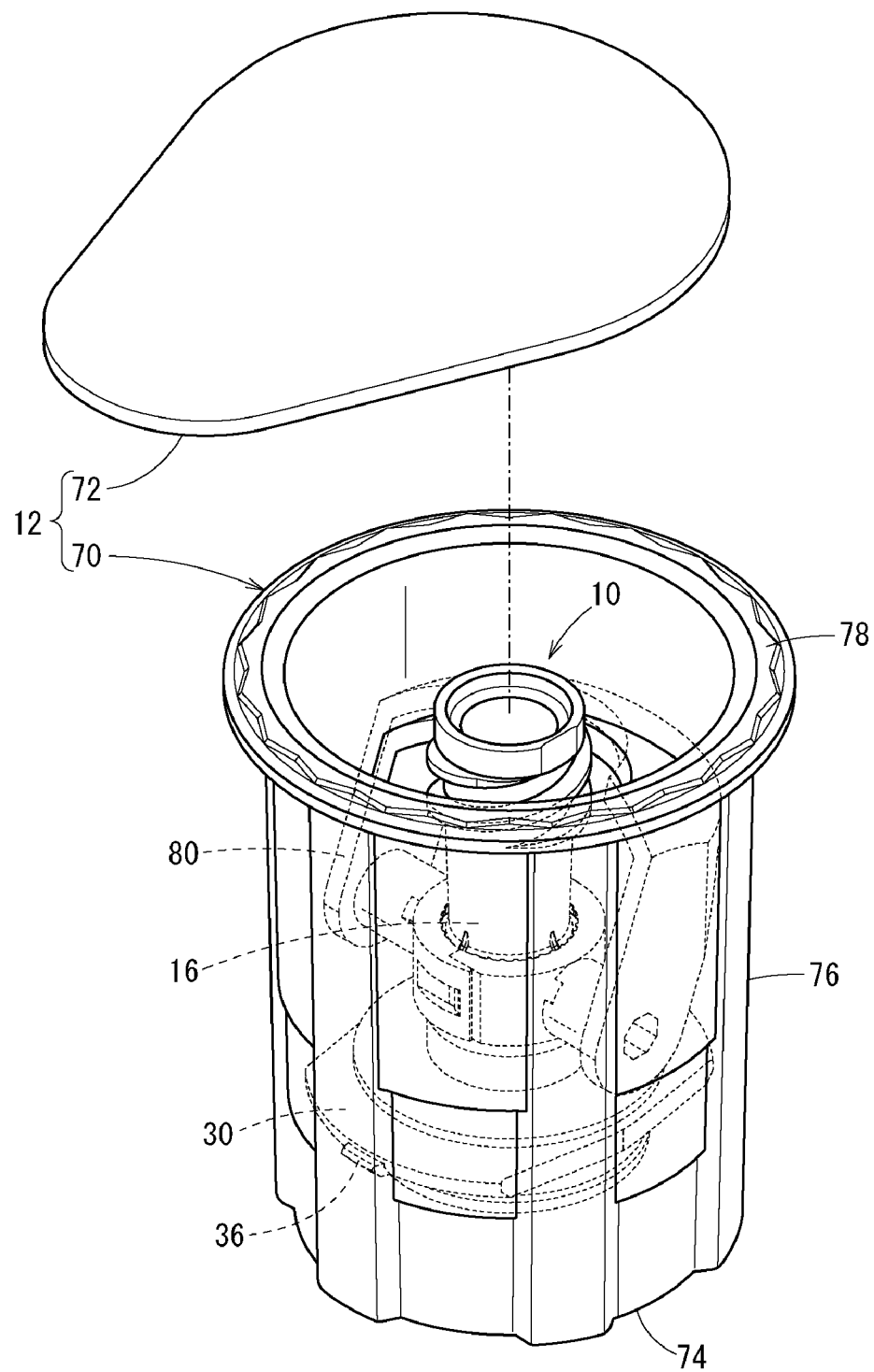
FIG. 1 is a perspective view illustrating a packaged article housing an intradermal needle according to a first embodiment.

An intradermal needle 10 of this embodiment is provided as a product as illustrated in FIG. 1, while being housed in a packaged article 12 that individually packages the intradermal needle (medical needle) 10. The intradermal needle 10, sealed in the packaged article 12, is kept aseptic until just before use.

The packaged article 12 includes a container 70 that houses the intradermal needle 10, and a seal member 72 that closes the container 70. When used, the seal member 72 is peeled off by the user from the container 70, thus making the intradermal needle 10 in the container 70 accessible to the user.

The container 70 possesses a cylindrical shape, with an inner space formed therein, and a bottom face 74 having a circular shape whose diameter is slightly larger than the diameter (outer diameter) of the wide diameter part (enlarged diameter part) 30 of the needle hub 16. The container 70 also includes an upstanding cylinder wall 76 that extends up from the bottom face 74 in the axial direction of the intradermal needle 10, and this cylinder wall 76 is sized so that an inner diameter of the container is slightly larger than the diameter (outer diameter) of the wide diameter part 30 of the intradermal needle 10. In the cylinder wall 76, an engagement part (not illustrated) that engages with a claw 36 of the wide diameter part 30 is formed. The engagement part and the claw 36 contribute to prevent disengagement of the intradermal needle 10 from the container 70, and to restrict pivoting of the intradermal needle 10 around the axis, making it easy to attach a syringe 20 (see FIG. 4). The top end of the cylinder wall 76 includes a flange 78 onto which the seal member 72 is bonded.

The intradermal needle 10 is housed in the packaged article 12, with the protector 80 held in the open position near the needle hub 16. Since the protector 80, in the open position, can fall within a cylindrical region having a diameter nearly equal to the diameter of the wide diameter part 30, the packaged article 12 sized according to the wide diameter part 30 can now house the intradermal needle 10.

Figure 4:
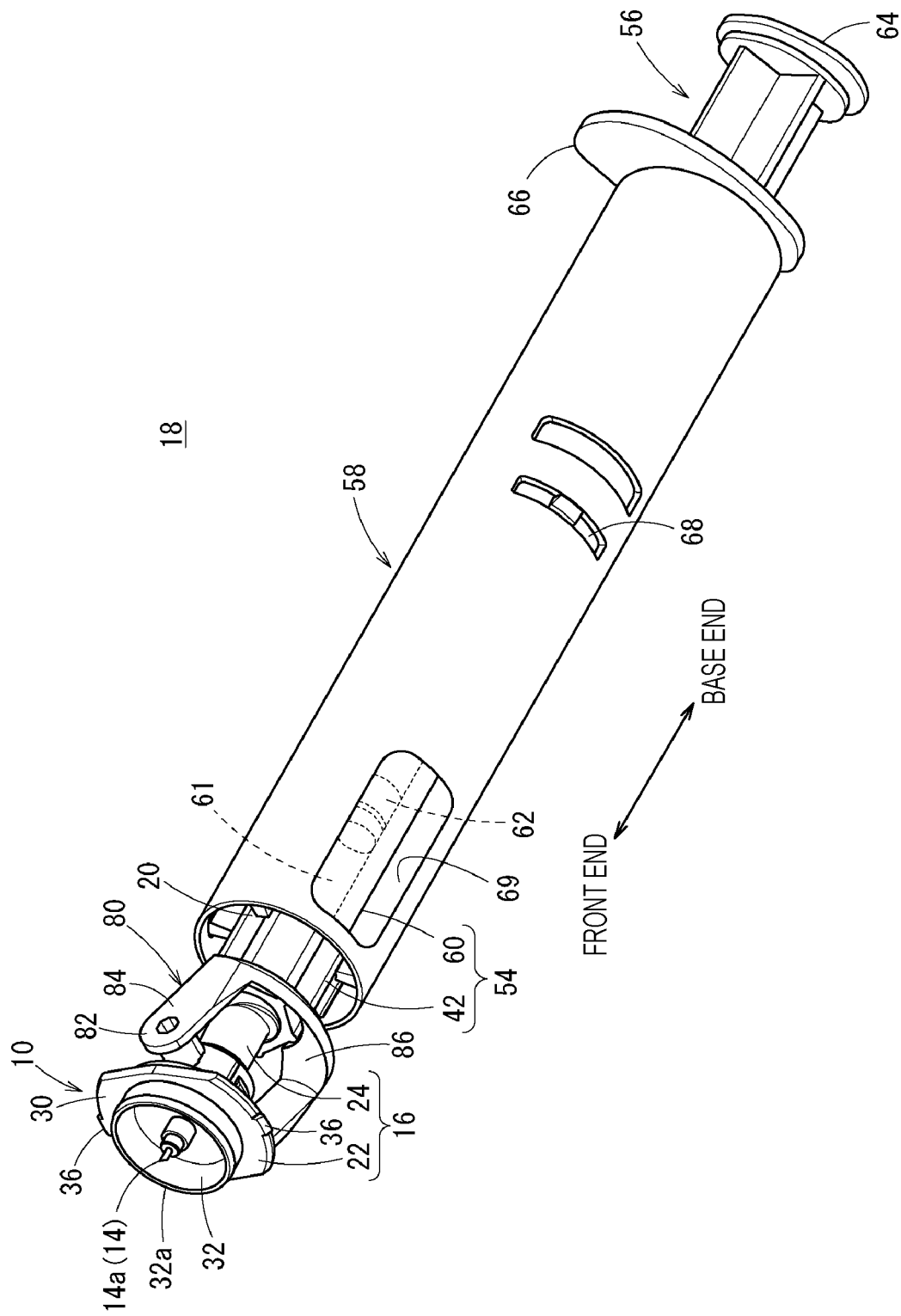
FIG. 4 is a perspective view illustrating an injection device having the intradermal needle according to the first embodiment.
Figure 6:
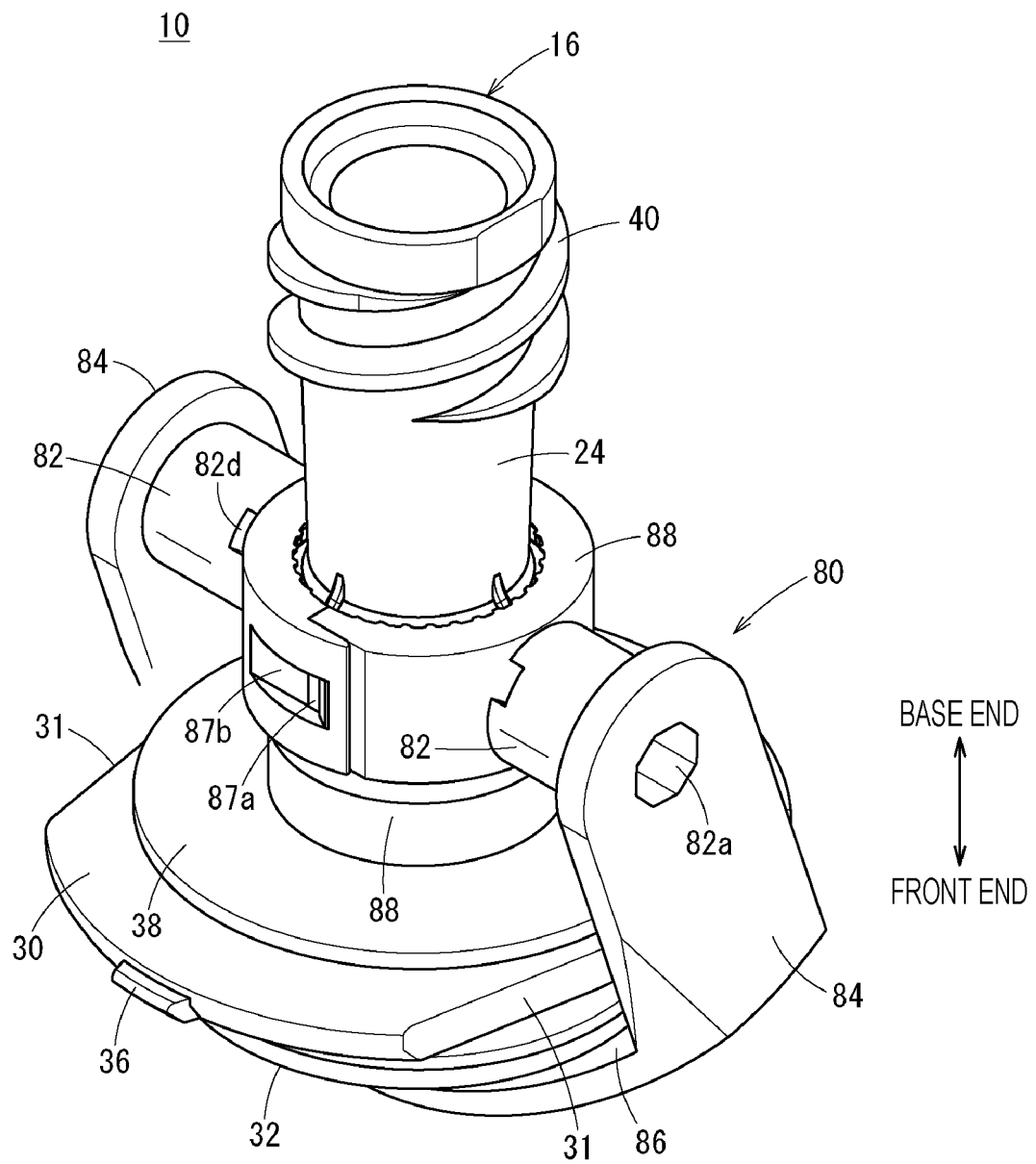
FIG. 6 is a perspective view illustrating the intradermal needle illustrated in FIG. 2, with the protector held in the closed position.

The intradermal needle 10 enclosed in the packaged article 12, with the protector 80 held in the open position, is used as it is in an injection device 18 (see FIG. 4). The intradermal needle 10 is designed so that the needle tip 14a is covered, after use, with the protector 80 by pivoting the protector 80 around the axle of pivoting (pivot axis or pivot axle) to the closed position as illustrated in FIG. 6.

Figure 2:
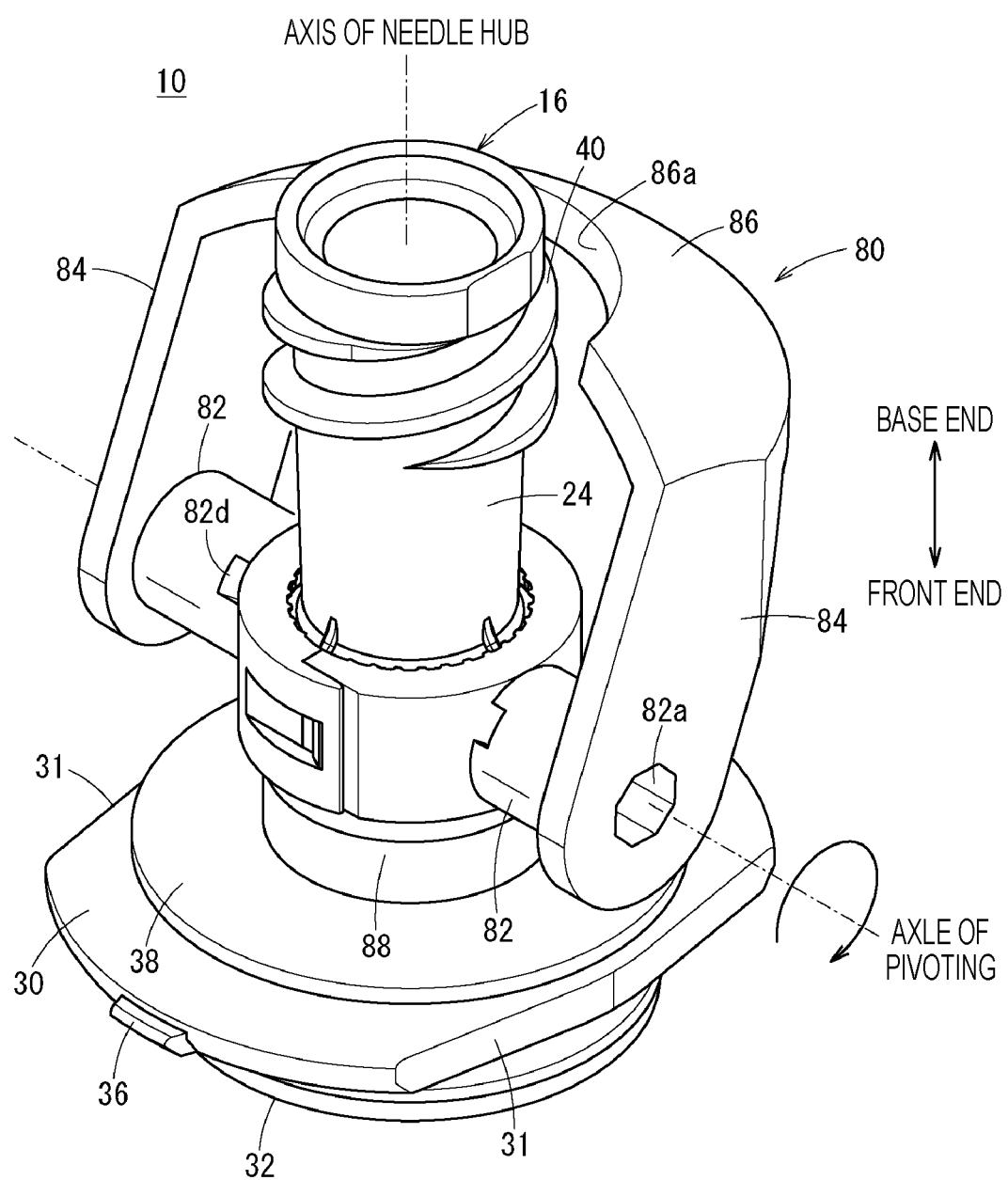
FIG. 2 is a perspective view illustrating the intradermal needle according to the first embodiment, with a protector held in the open position.

Next, a structure of the protector 80 constituting a part of the intradermal needle 10 will be explained. The protector 80 has, as illustrated in FIG. 2, a pair of connection parts 82, an arm 84 that extends from each of the connection parts 82, a lid 86 supported by the pair of arms 84, and a bracket 88 mounted on a second member 24 of the needle hub 16. In the description below, the direction approaching the axis of the needle hub 16 is referred to as inner or inside, while the direction departing from or moving away from the axis is referred to as outer or outside. Also, a face closer to the axis of the needle hub 16 is referred to as an inner circumferential face, while a face on the side departing from the axis is referred to as an outer circumferential face.

Figure 3:
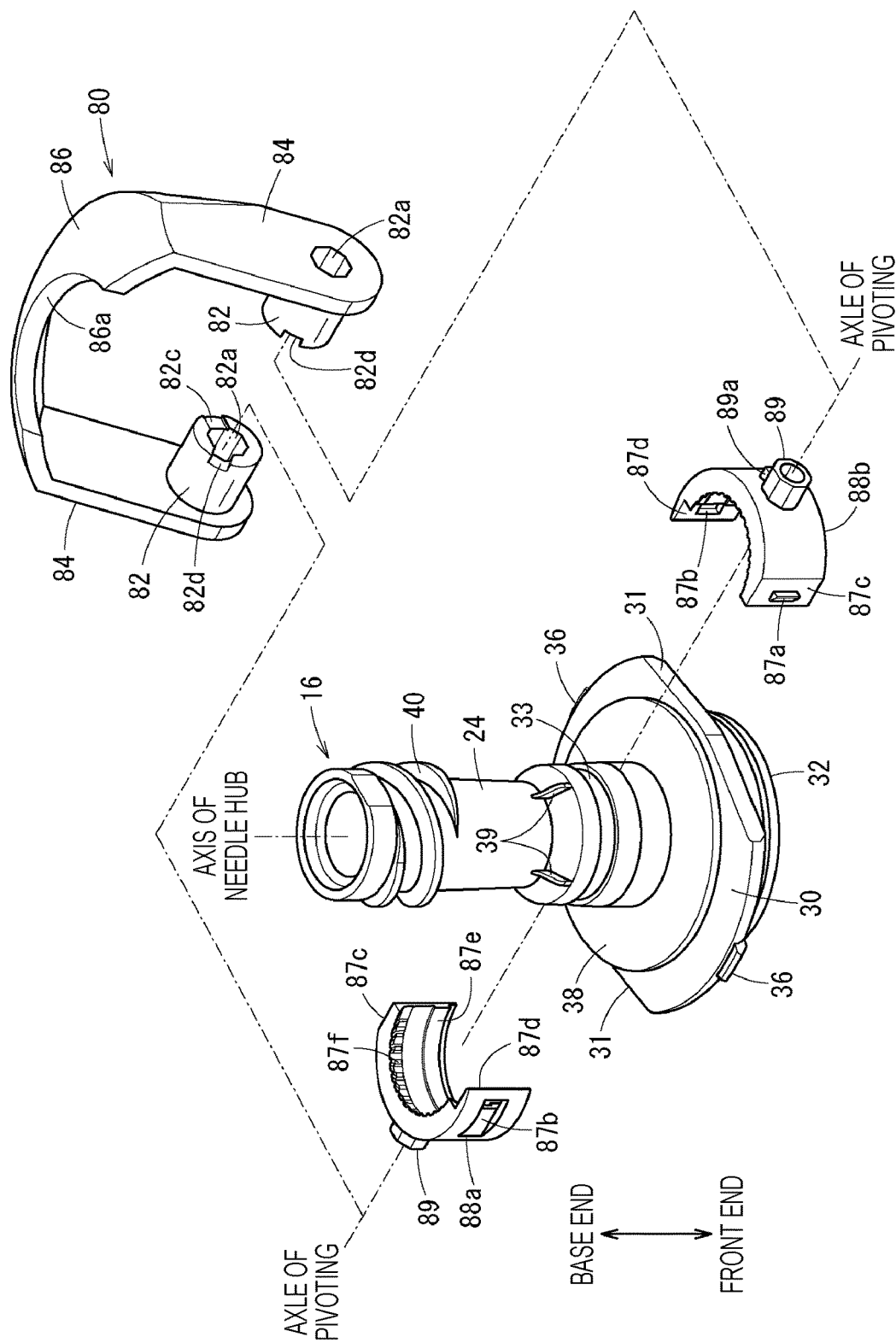
FIG. 3 is an exploded perspective view illustrating the protector illustrated in FIG. 2.

The bracket 88 is a cylindrical component that holds the second member 24 between from the outer circumferential side. As illustrated in FIG. 3, the bracket 88 is composed of halves, which are a split piece 88a and a split piece 88b. Each of the split piece 88a and the split piece 88b has a connection part having a wedge 87c thinned towards the end, and a receiving part 87d that receives the wedge 87c. The wedge 87c is provided with a stopper piece 87a for preventing unintentional release, and a hole 87b that engages with the stopper piece 87a is formed in the receiving part 87d. The split pieces 88a, 88b are engaged with each other by inserting the wedges 87c of the split pieces 88a, 88b into the receiving parts 87d, and by engaging the stopper pieces 87a with the holes 87b, thereby the bracket 88 is mounted so as to hold the second member 24 in between.

Each of the split pieces 88a, 88b has a ring-shaped protrusion 87e formed on the inner circumferential face, and a plurality of ribs 87f arranged at intervals in the circumferential direction on the inner circumferential face. The protrusion 87e, when fitted in a groove 33 formed in a side wall of the second member 24, blocks the bracket 88 from moving towards the front end or the base end. With the bracket 88 mounted on the second member 24, the ribs 87f engage with pivoting stop protrusions 39 that extend from the outer circumference of the second member 24 in radial directions. Rotation of the bracket 88 around the axis of the needle hub 16 may thus be blocked by the engagement between the pivoting stop protrusions 39 and the ribs 87f.

Each of the split pieces 88a, 88b has, on the outer circumferential face and at the center thereof in the circumferential direction, an axle pin 89 (pivoting axle part) formed so as to extend outwards. The axle pin 89 on one split piece 88a is arranged at an opposite position 180 degrees from the axle pin 89 on the other split piece 88b, while the second member 24 is positioned between the two axle pins, and the center axis of these axle pins 89 extends perpendicularly to and passes through the axis of the second member 24. The axle pins 89 are members that support the connection parts 82, whose center axis serves as a pivot axis or rotation axis of the protector 80. The center axis (axle of pivoting or axis of rotation) of the axle pins 89 need not always be perpendicular to and pass through the axis of the needle hub 16, and instead may be in the vicinity of the axis of the needle hub 16, meaning the axis of rotation can be slightly spaced from the needle hub 16 axis.

Each axle pin 89 possesses a polygonal (non-circular) shape, and is slidable against a hole 82a that also possesses a polygonal shape. This produces resistive force that acts to obstruct pivoting motion of the protector 80, and blocks free pivoting of the protector 80. That is, the polygonal outer circumferential faces of the axle pins 89 and the polygonal holes 82a constitute the resisting member, by which the protector 80 is prevented from unintentionally pivoting.

The axle pin 89 has a restriction projection 89a that extends from the outer side face of the axle pin 89. The restriction projection 89a engages with an open position restriction groove or recess 82c and a closed position restriction groove or recess 82d of each connection part 82 and can thereby stop or hold the protector 80 in the open position or in the closed position. That is, the restriction projection 89a, the open position restriction groove 82c and the closed position restriction groove 82d constitute the restriction member.

In the protector 80, the connection part 82, the arm 84 and the lid 86 are formed integrally in one piece. Each of the connection part 82 and the arm 84 is provided as a pair, and the lid 86 is supported from both sides by the pair of arms 84. The connection part 82 is provided as a pair, corresponding to the axle pins 89. Each connection part 82 possesses a cylindrical shape that extends in the direction of the pivot axis, and has at the center thereof a hole 82a that engages with each axle pin 89. The connection parts 82 are attached to the bracket 88, by fitting the connection parts 82 having the holes 82a on the axle pins 89 from outside. Each hole 82a has a polygonal inner circumferential face, so as to produce resistive force against the axle pin 89 in the direction of pivoting.

Each connection part 82 has the open position restriction groove 82c and the closed position restriction groove 82d formed at the inner end of the connection part 82 (the end face remote from the arms 84). The open position restriction groove 82c engages with the restriction projection 89a of the axle pin 89, when the protector 80 is in the open position. This makes the protector 80 stop in the open position (i.e., the protector 80 is held in the open position). That is, as a result of engagement of the restriction projection 89a with the open position restriction groove 82c, the protector 80 is restricted from pivoting away from the open position. Meanwhile, the closed position restriction groove 82d engages with the restriction projection 89a of the axle pin 89, when the protector 80 is pivoted to the closed position where the lid 86 covers the needle tip 14a of the tubular needle 14 (see FIG. 6). That is, as a result of engagement of the restriction projection 89a with the closed position restriction groove 82d, the protector 80 is restricted from pivoting away from the closed position.

The arm 84 extends from the end of the outer circumference of the connection part 82, towards the outside of the pivot axis. The length of the arm 84 is determined to an extent that the lid 86 will not interfere with or contact the wide diameter part 30, when the protector 80 is pivoted to the closed position. In addition, the interval (distance in the direction of the pivot axis) between the one arm 84 and the other arm 84 is determined smaller than the diameter of the wide diameter part 30 (but excluding the cutout side 31). With such structure, the protector 80 may be downsized, and the intradermal needle 10 may be housed within a cylindrical range having a diameter nearly equal to the diameter of the protector 80, with the protector 80 held in the open position.

The wide diameter part 30 has a pair of cutout sides 31 formed conforming to the interval or distance between the arms 84. As shown in FIG. 3, the periphery of the wide diameter part 30 may thus be defined by the straight cutout sides 31 connected by curved segments. These cutout sides 31 are formed inside the inner face of the arms 84, and extend in the direction of pivoting of the arms 84. The wide diameter part 30 is thus designed not to obstruct pivoting of the arms 84. As shown in FIG. 3, dimension of the wide or enlarged diameter part 30 (flange) is smaller in the direction parallel to the axle of pivoting (pivot axis) than in the direction perpendicular to the axle of pivoting (pivot axis).

The lid 86 is formed so as to lie across the pair of arms 84. At the center of the lid 86, a semicircular cutout 86a is formed by performing semicircular cutting out operation. The cutout 86a is formed so as to eliminate a part of the lid 86 which comes near the axis of the second member 24 when the protector 80 is held in the open position. With the cutout 86a thus provided, there is produced, as illustrated in FIG. 2, a gap between the male screw 40 of the second member 24 and the lid 86, into which the front end of the syringe 20 (see FIG. 5) can be inserted. The lid 86 may alternatively be formed to give a curved face as illustrated in FIG. 3, without special limitation.

The aforementioned protector 80 may be attached according to the procedures below. First, there is provided the needle hub 16 whose wide diameter part 30 has preliminarily formed therein the cutout sides 31 and the groove 33. The split pieces 88a, 88b are then positioned in predetermined directions relative to the second member 24 of the needle hub 16, and mounted on the second member 24 so as to hold the second member 24 or be held on the second member 24 from the outer circumferential side, to build up or construct the bracket 88. Next, the connection part 82 is brought, with the arms 84 stretched apart, close to the axle pins 89 of the bracket 88, and the axle pins 89 are inserted into the holes 82a of the connection part 82, to build up or construct the protector 80. The protector 80 is then suitably pivoted to engage the restriction projections 89a with the open position restriction groove 82c to thereby fix the protector 80 in the open position. Attachment of the protector 80 is thus finished. The thus manufactured intradermal needle 10 is enclosed or packaged in the packaged article 12 (see FIG. 1), and marketed as a product.

The injection device 18 having the intradermal needle 10 will be explained below, featuring an internal structure of the intradermal needle 10. The intradermal needle 10 has, as illustrated in FIG. 4, a tubular needle 14 and a needle hub 16, and composes a component of an injection device 18. When used, the intradermal needle 10 is assembled on a syringe 20 provided separately from the intradermal needle 10. The user attaches the syringe 20 to the intradermal needle 10 to assemble the injection device 18, and then punctures a living body with the needle tip 14a of the intradermal needle 10. Upon pressing a plunger 56 of the syringe 20 while maintaining the punctured state, a chemical solution contained in the syringe 20 is intradermally injected through the tubular needle 14 into the living body.

After injection, the intradermal needle 10 is disposed, with the used tubular needle 14 covered and unexposed by the protector 80, thus making it possible to avoid accidental puncture with the tubular needle 14. The individual components of the injection device 18 (intradermal needle 10 and syringe 20) will be explained below.

Figure 5:
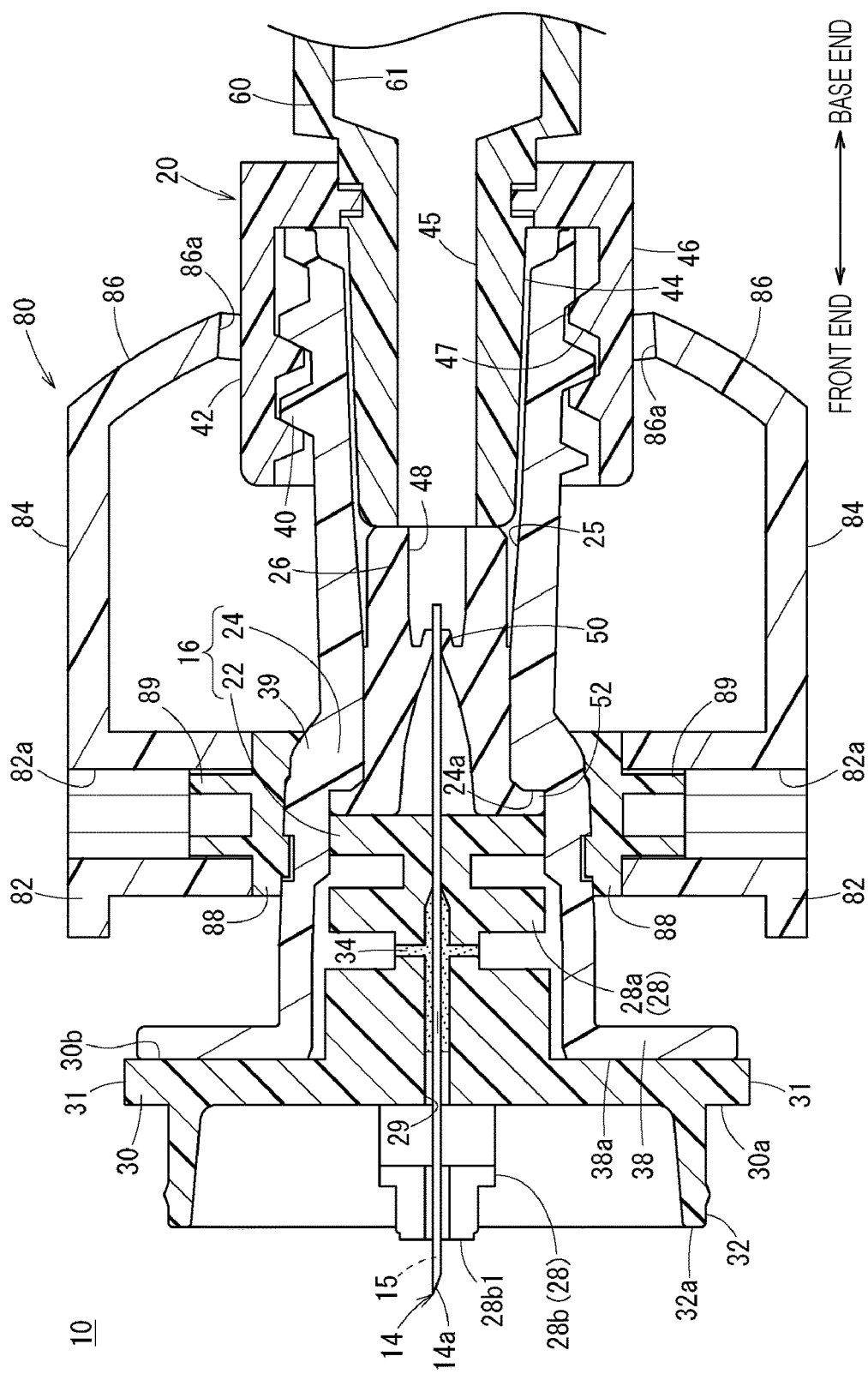
FIG. 5 is a cross-sectional view illustrating the intradermal needle illustrated in FIG. 2, with a syringe attached to the intradermal needle.

As illustrated in FIG. 5, the tubular needle 14 of the intradermal needle 10 is given in the form of rigid hollow tube, with a needle hole 15 arranged at the axial center. A needle tip 14a having a sharp blade face or pointed end is at the frontmost part (distal-most end) of the tubular needle 14. The tubular needle 14 may have a diameter not specifically limited, whose gauge number is typically 26 to 33 (0.2 to 0.45 mm), and more preferably 30 to 33. Examples of materials from which the tubular needle 14 may be fabricated include stainless steel, aluminum, aluminum alloy, titanium, titanium alloy, other metals, and hard resins.

The needle hub 16 of the intradermal needle 10 has a first member 22 to which the tubular needle 14 is fixed, and a second member 24 on which the syringe 20 to be attached to the first member 22 is assembled. Examples of materials from which the first and second members 22, 24 may be fabricated include resin materials such as polycarbonate, polypropylene, and polyethylene. The needle hub 16 also has an elastic member 26 inside the second member 24.

The first member 22 has an axial part 28 that directly holds the tubular needle 14, the wide diameter part 30 that extends radially outward from the outer circumferential face of the axial part 28, and an axially extending annular or ring-shaped protrusion 32 that extends ahead of an end face 30a of the wide diameter part 30. The axial part 28 possesses a near cylindrical shape, and, at the axial center of the axial part 28, is provided with a fixing hole 29 that houses and fixes the tubular needle 14. With the tubular needle 14 positioned in the fixing hole 29, an adhesive 34 is injected to fix the tubular needle 14 and the first member 22.

The axial part 28 has a housing part 28a housed in the second member 24, and a protruding part 28b that protrudes ahead of the wide diameter part 30. The protruding part 28b of the axial part 28 protrudes slightly ahead of the ring protrusion 32, and has an end face 28b1 that comes into contact with a surface of a living body. The tubular needle 14 fixed to the fixing hole 29 protrudes an appropriate amount (length of protrusion) ahead of the end face 28b1. For example, the length of protrusion of the tubular needle 14 is designed equivalent to the depth of dermis from the skin surface of the living body, which preferably falls in the range from approximately 0.5 to 3.0 mm.

The wide diameter part 30 is formed like a disk that extends from the outer circumferential face of the axial part 28 in the direction perpendicular to the center axis of the axial part 28. The wide diameter part 30 extends further beyond the ring protrusion 32 in the radial direction. On the base end face or surface 30b, which is a face or surface on the base end side of the wide diameter part 30 (a face opposite to the end face 30a at which the annular protrusion 32 is arranged), the second member 24 is bonded. As illustrated in FIG. 4, on the outer circumference of the wide diameter part 30, a pair of claws 36 are formed so as to protrude outward. The pair of claws 36 are arranged on the opposite sides (180° degrees opposite position) on the outer circumference of the wide diameter part 30.

The annular or ring-shaped protrusion 32 is a part that slightly protrudes like a wall from the wide diameter part 30 towards the front end, and is configured to define a cylindrical shape that surrounds the axial part 28 while maintaining a predetermined distance in between. When using the intradermal needle 10, the entire range of an end face 32a of the ring protrusion 32 comes into contact with the skin of the living body. The ring protrusion 32 can therefore guide the injection device 18 so as to maintain the puncture posture perpendicular to the skin, and can maintain a constant depth of penetration of the tubular needle 14 into the skin.

As illustrated in FIG. 5, the second member 24 is configured as a near cylindrical shape with a through-hole 25 formed along the center axis. On the front end side of the through-hole 25, the housing part 28a of the first member 22 is positioned, meanwhile in the middle of the through-hole 25, an elastic member 26 is housed. On the base end side of the through-hole 25, a nozzle 44 of the syringe 20 is inserted during assemblage of the injection device 18. The inner circumferential face, on the base end side, of the through-hole 25 is tapered so as to allow surface contact with the outer circumferential face of the nozzle 44.

On the front end of the second member 24, there is provided a connecting wide diameter part 38 that extends outwards in the radial direction. The outer circumferential edge of the connecting wide diameter part 38 is inside the outer circumferential edge of the wide diameter part 30 of the first member 22. The connecting wide diameter part 38 is fixed at its end face 38a to the base end face 30b of the wide diameter part 30, by an appropriate method of bonding such as vibration welding. On the outer circumferential face or surface on the base end side of the second member 24, there is provided a male screw 40 on which a female screw 47 of the syringe 20 is screwed.

In other words, the syringe 20 has in its front end part 42, a nozzle 44 having an ejection channel 45 communicated with a reservoir 61 of the drug, and a connector 46 arranged around the nozzle 44, with the female screw 47 threaded on the inner face. With the male screw 40 and the female screw 47 engaged, the end face of the nozzle 44 comes into contact with, and pressurizes the base end face of the elastic member 26.

The elastic member 26 of the intradermal needle 10 is a cylindrical connecting or joining member that keeps the base end of the tubular needle 14 liquid-tight, and holds the needle hole 15 opposing to the ejection channel 45 of the nozzle 44. The elastic member 26 includes a tubular needle hole 48, and in the tubular needle hole 48, an inner projection 50 that holds the inserted tubular needle 14 in contact therewith is formed. The elastic member 26 is tightly fixed while fitting itself to the inner circumference of the through-hole 25 of the second member 24, and while allowing an outward projection 52, which projects at the front end side outwards in the radial direction, to be positioned or held between the base end face of the first member 22 and a step 24a of the second member 24.

The bracket 88 is mounted on the outer circumferential surface of the second member 24. The bracket 88 is provided with the pair of axle pins 89. The axle pins 89 are arranged at 180 degrees opposite positions on the outer circumference of the bracket 88. The axle pins 89 are individually fitted with the connection parts 82 having the holes 82a. Each connection part 82 protrudes outwards by a predetermined length. From each connection part 82, each arm 84 extends. The lid 86 is formed or provided at the free ends of such pair of arms 84. The lid 86 has the cutout 86a that produces, between the lid 86 in the open position and the needle hub 16, the gap into which the syringe 20 can be inserted. That is, provision of the cutout 86a enables attachment of the syringe 20 to the needle hub 16, without interference from the protector 80 even when the protector 80 is housed in the open position near the axis of the needle hub 16.

Meanwhile, the syringe 20 of the injection device 18 illustrated in FIG. 4 is provided as a prefilled syringe having the drug preliminarily filled therein. The syringe 20 has a syringe body 54, a plunger 56 that is positioned in the syringe body 54 in a relatively movable manner, and a holder 58 that covers the outside of the syringe body 54.

The syringe body 54 has the front end part 42 (nozzle 44 and connector 46), and a barrel 60 having a reservoir 61 that communicates with the front end part 42 and stores the drug. A gasket 62 is provided at the front end of the plunger 56. The gasket 62 is positioned in a liquid-tight manner in the reservoir 61, and has at the base end of the gasket 62 an operation part 64 pushed by the user of the injection device 18. Alternatively, the syringe 20 may be of a type having the gasket 62 preliminarily housed in the reservoir 61, allowing the plunger 56 to be attached to the gasket 62 when the syringe 20 is used.

The holder 58 is a cylindrical body that houses and fixes the syringe body 54, and is used for increasing the outer diameter of the injection device 18, making it more convenient for the user to grip. Hence the holder 58 has on the base end thereof a finger flange 66 on which fingers of the user who pushes the operation part 64 of the plunger 56 are hooked or engaged. The injection device 18 may alternatively have no holder 58.

The inner wall of the holder 58 surrounding the inner space has a plurality of support pieces (not illustrated) that support the front end part of the barrel 60 of the syringe body 54. The outer circumference of the holder 58 also has a lock window 68 that locks a flange (not illustrated) provided to the base end of the syringe body 54, and the holder 58 also has at around the front end thereof a check window 69 through which the reservoir 61 of the syringe body 54 can be visually checked.

The intradermal needle 10, the packaged article 12, and the injection device 18 according to this embodiment are basically composed as described above. Operations of these items will be explained below.

The intradermal needle 10 is marketed as a product as illustrated in FIG. 1, while being enclosed in the container 70 of the packaged article 12. As described above, the intradermal needle 10 in this state has the protector 80 held in the open position near the axis of the needle hub 16. The packaged article 12 keeps the intradermal needle 10 airtight, by virtue of the seal member 72 bonded to the flange 78 of the container 70.

When using the injection device 18, the seal member 72 of the packaged article 12 is peeled off, and the front end of the syringe 20 is inserted into the packaged article 12, so as to connect the base end of the intradermal needle 10 and the syringe 20. That is, as illustrated in FIG. 4, the nozzle 44 of the front end part 42 of the syringe 20 is inserted into the through-hole 25 of the second member 24, and the female screw 47 of the connector 46 is screwed on the male screw 40 of the intradermal needle 10. In this process, the protector 80 of the intradermal needle 10 is kept in the open position as illustrated in FIG. 5. The connector 46 of the syringe 20 is inserted in the gap between the semicircular cutout 86a formed in the lid 86 of the protector 80 and the second member 24.

After the intradermal needle 10 and the syringe 20 are connected, the syringe 20 is pulled out from the packaged article 12. In this way, the pair of claws 36 of the intradermal needle 10 are released from the packaged article 12, and thereby the intradermal needle 10 and the syringe 20 are integrally taken out from the packaged article 12.

The tubular needle 14 of the intradermal needle 10 is then punctured into the living body to inject the drug stored in the reservoir 61 of the syringe 20. The protector 80 in this state is held in the open position, while keeping the open position restriction groove 82c of the connection part 82 engaged with the restriction projection 89a. After injecting the drug, the used intradermal needle 10 is removed from the living body and is disposed.

When disposing the intradermal needle 10, the user pivots the protector 80 with fingers to the closed position. In this process, upon application of a predetermined level or larger force in the direction of pivoting of the protector 80 towards the closed position, the arms 84 will elastically deform outwards, and the restriction projections 89a are released from the open position restriction grooves 82c to thereby allow the arms 84 to freely pivotable. Upon further pivoting of the protector 80 towards the closed position, the restriction projections 89a engage the closed position restriction grooves 82d (see FIG. 3) of the connection part 82, thus the protector 80 stops pivoting. The protector 80 thus moves to the closed position. In the closed position, the protector 80 is held so as not to escape the closed position, as a result of engagement of the restriction projections 89a with the closed position restriction grooves 82d of the fixed connection part 82. With the needle tip 14a of the tubular needle 14 thus covered by the lid 86 of the protector 80, the user is protected from the sharp needle tip 14a. Thus the intradermal needle 10 can be disposed safely.

As described above, the intradermal needle 10 of this embodiment has the pivoting axle part (axle pin 89) of the protector 80 provided on the bracket 88 which is mounted on the base end side of the wide diameter part 30. This makes the protector 80 movable by pivoting nearly centered round the needle hub 16, and thereby the protector 80 may be housed compactly in the open position near the needle hub 16. This makes it possible to house the intradermal needle 10 with the protector 80 within the packaged article 12 whose inner diameter is nearly equal to the diameter (outer diameter) of the wide diameter part 30.

The protector 80 is designed to include the pair of connection parts 82 and the pair of arms 84 arranged while placing the second member 24 in between, and to make the pair of arms 84 support the lid 86 from both sides. This enhances strength of the protector 80, makes it less likely to deform under force applied from directions other than direction of pivoting, and makes the protector 80 pivotable safely to the closed position.

In the wide diameter part 30 of the needle hub 16, the cutout sides 31 that extend in the direction of pivoting of the arms 84 are formed. With such structure, the wide diameter part 30 may be prevented from coming into contact with the arms 84 during pivoting operation of the arms 84. The interval between the pair of arms 84 may be made smaller than the outer diameter of the wide diameter part 30, which is variable depending on position of the cutout sides 31. This makes it possible to house the protector 80 with the arms 84 compactly in the open position, improving convenience for housing in a small packaged article 12.

The protector 80 is provided with the open position restriction grooves 82c, the closed position restriction grooves 82d, and the restriction projections 89a that engage the open position restriction grooves 82c and the closed position restriction grooves 82d, all of which constitute a restriction member for restricting pivoting at the open position and the closed position. This successfully restricts pivoting of the protector 80 enclosed in the packaged article 12, and prevents accidental contact of the lid 86 in the open position with the syringe 20. It also makes it possible to prevent the protector 80 in the closed position from pivoting, and allowing the needle tip 14a to accidentally be exposed.

With the cutout 86a in the lid 86 in a part closer to the pivot axis, formed so as to eliminate a part thereof near the axis of the second member 24, a space is now available for insertion of the syringe 20.

In the intradermal needle 10, the annular bracket 88 is mounted on the second member 24, and the axle pins 89 are arranged to the bracket 88. Hence the axle of pivoting of the protector 80 approaches near the axis of the needle hub 16, and the protector 80 in the open position can be housed near the needle hub 16, thus improving convenience for housing of the intradermal needle 10.

Second Embodiment

An intradermal needle 10A of a second embodiment will be explained below. The inner structure of the needle hub 16 of the intradermal needle 10A is the same as that of the intradermal needle 10 illustrated in FIG. 5, and so a detailed description of such inner structure will not be repeated. In the description below, structure and features of the intradermal needle 10A that are the same as those in the intradermal needle 10 described above and illustrated in FIGS. 1-6 are identified by the same reference numerals and a detailed description of such structure and features is not repeated.

Figure 7:
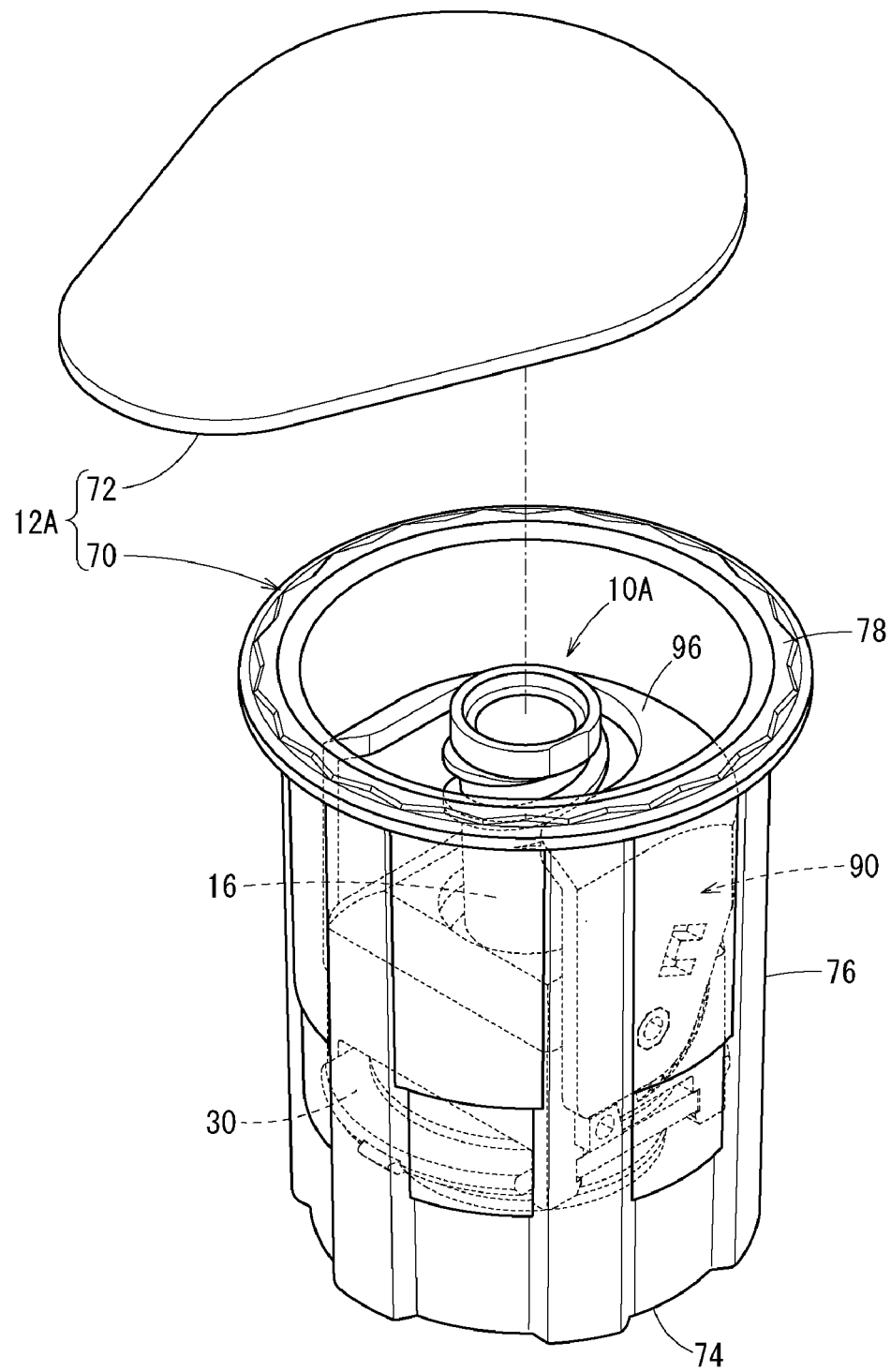
FIG. 7 is a perspective view illustrating a packaged article housing an intradermal needle of a second embodiment.

The intradermal needle 10A is marketed as a product enclosed in the packaged article 12A, with a lid 96 of a protector 90 held in the open position near the axis of the needle hub 16, as illustrated in FIG. 7. The packaged article 12A includes a container 70 with a housing space for housing the intradermal needle 10A, and a seal member 72 that seals the container 70. The container 70 has a bottom face 74 whose inner diameter is nearly equal to the diameter (outer diameter) of the wide diameter part 30 of the intradermal needle 10A, and from the bottom face 74, the cylindrical cylinder wall 76 extends in the axial direction of the intradermal needle 10A. The cylinder wall 76 has an inner diameter nearly equal to the diameter (outer diameter) of the wide diameter part 30. The cylinder wall 76 has the flange 78 at the top end of the cylinder wall 76, and the seal member 72 is bonded to the flange 78.

Figure 8:
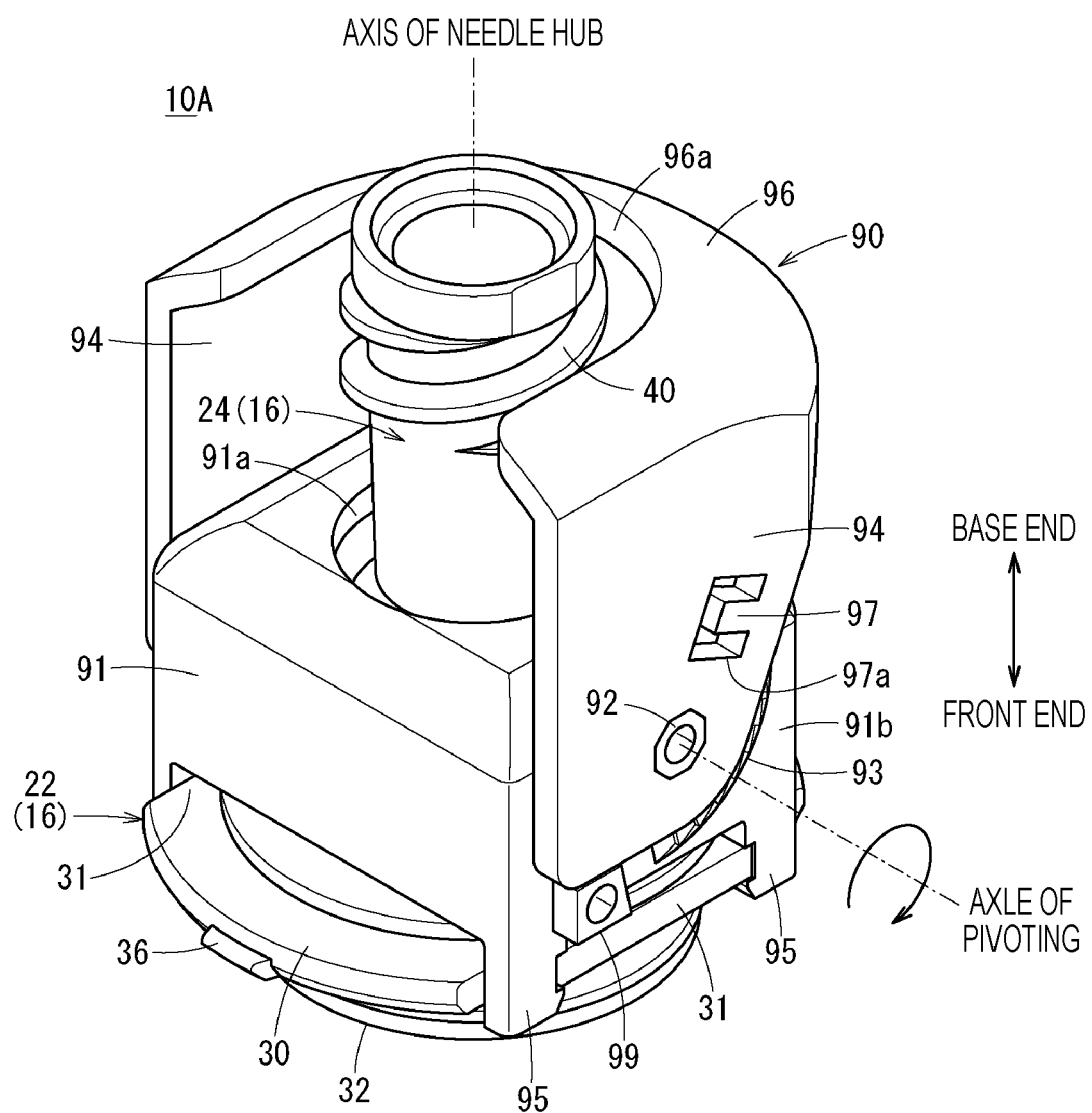
FIG. 8 is a perspective view illustrating the intradermal needle according to the second embodiment, with a protector held in the open position.

The intradermal needle 10A of this embodiment is composed of, as illustrated in FIG. 8, the needle hub 16 having the first member 22 and the second member 24, and the protector 90 mounted thereon. The protector 90 has a socket 91 mounted so as to cover the wide diameter part 30 from the base end side, the pair of arms 94 attached to the socket 91, and the lid 96 supported by the arms 94.

The protector 90 of this embodiment has the axle of pivoting (pivot axis) positioned on the base end side of the wide diameter part 30, and the axle of pivoting (pivot axis) extends in the direction perpendicular to the axis of the needle hub 16. The axle of pivoting of the protector 90 preferably lies perpendicular to and passes through the axis of the needle hub 16, but may be positioned slightly spaced from the needle hub 16 axis so as to lie near the axis of the needle hub 16. This enables the protector 90 to pivot nearly centered round the needle hub 16, and thereby the lid 96 in the open position may be housed compactly near the needle hub 16.

Figure 9:
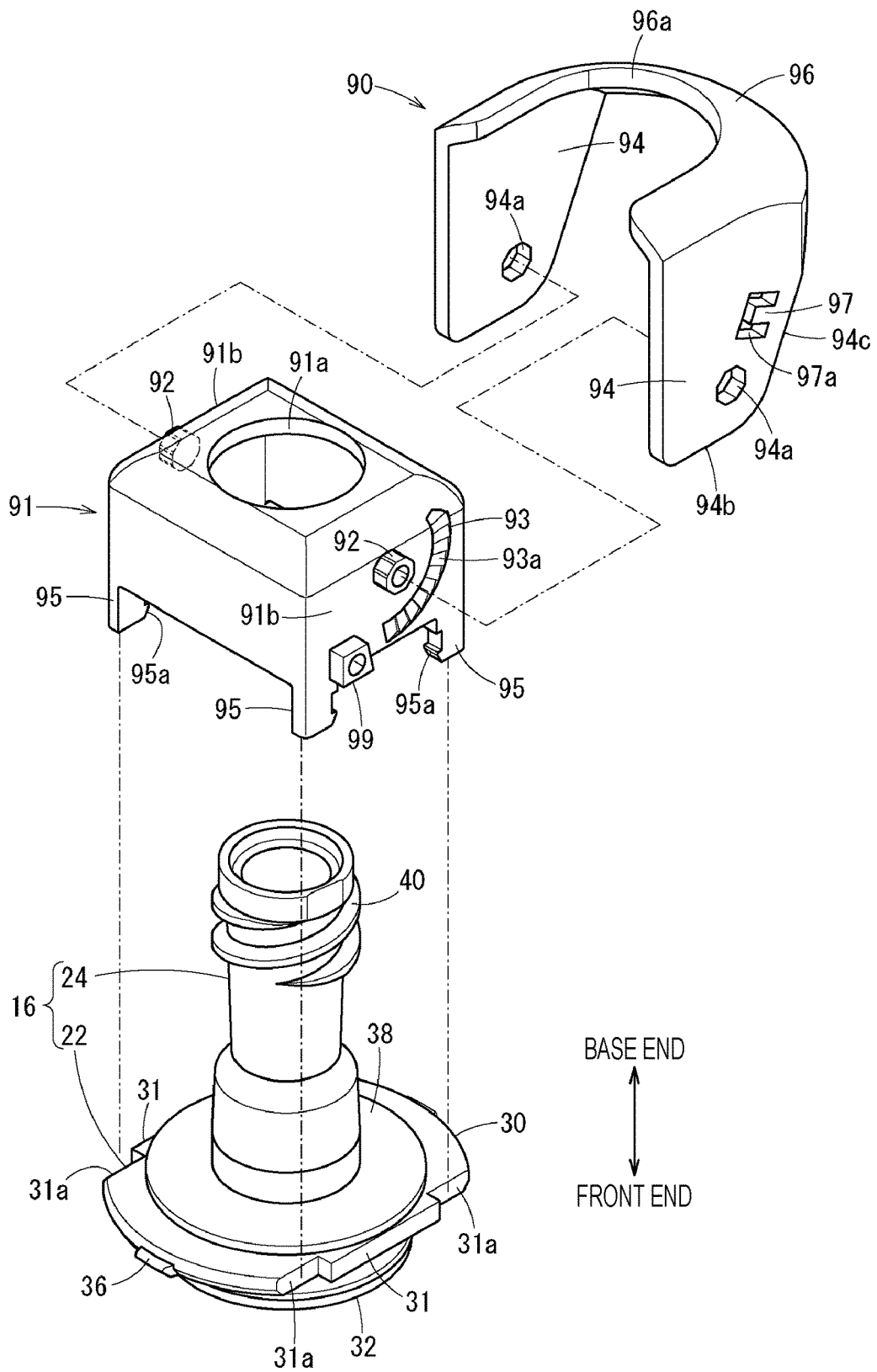
FIG. 9 is an exploded perspective view illustrating the protector illustrated in FIG. 8.

The socket 91 of the intradermal needle 10A is mounted on the wide diameter part 30 of the first member 22. The wide diameter part 30 has the pair of cutout sides 31 formed so as to cut out, in a straight or linear manner, in the direction of pivoting of the protector 90. These cutout sides 31 are formed on the pivoting face 91b of the socket 91 in a co-plane manner, so as not to interfere with the pivoting of the arms 94. As illustrated in FIG. 9, on both ends of cutout side 31, recesses 31a on which legs 95 of the socket 91 are engaged are formed. The legs 95 of the socket 91 engage their hooks 95a with the recesses 31a, to thereby mount the socket 91 on the wide diameter part 30.

The socket 91 is shaped like a box with an open end on the front end side, and has the legs 95 extended from four corners thereof on the front end side. Each leg 95 has the hook 95a that engages with the wide diameter part 30. By fitting the legs 95 with the recesses 31a of the wide diameter part 30 to thereby engage the hooks 95a with the wide diameter part 30 as described above, the socket 91 is fixed on the needle hub 16. The upper face of the socket 91, on the base end side, also has a circular opening 91a. The opening 91a is larger than the outer diameter of the second member 24 of the needle hub 16. With the second member 24 allowed to pass through the opening 91a, the socket 91 is mounted on the wide diameter part 30 without coming into contact with the sidewall of the second member 24.

Among the four side faces of the socket 91, a pair of pivoting faces 91b that are opposed to the arms 94 individually have the axle pins 92 that compose the pivoting axle part. Each axle pin 92 extends like a pillar in the direction perpendicular to the axis of the needle hub 16, whose center axis serves as the axle of pivoting (pivot axis) of the protector 90. Each axle pin 92 has a polygonal shape when viewed from the direction of the pivot axis, and is designed to produce a predetermined level of resistive force against pivoting of the arms 94. Such axle pin 92 is also provided to the pivoting face 91b on the far side of the sheet of drawing, and these axle pins 92 are arranged on a common pivot axis, meaning the pivot axes for the two axle pins 92 are coaxial.

The pivoting face 91b also has an arcuate ratchet groove 93 centered round the axle of pivoting (i.e., the center of the radius of curvature of each arcuate ratchet groove 93 is the pivot axis of the axle pin 92 on the respective side of the socket), and a protrusion part 99 arranged on an extension ahead of one end of the ratchet groove 93. The ratchet groove 93 is a part engaged with the claw 97 of the arm 94, and the claw 97 is designed to move, as the arm 94 pivots, along the ratchet groove 93 while keeping contact with the ratchet groove 93 towards the protrusion part 99. In the ratchet groove 93, a plurality of teeth 93a are formed. These teeth 93a are formed to give a saw-shaped cross section with upright faces on the side closer to the protrusion part 99.

The protrusion part 99 also functions as the open position restriction member and the closed position restriction member. That is, upon contact of the protrusion part 99 with a first side edge 94b of the arm 94, the arm 94 is restricted from further pivoting in the open direction (i.e., in the counter-clockwise direction in FIG. 8). Meanwhile, upon contact of the protrusion part 99 with a second side edge 94c of the arm 94, the arm 94 is restricted from further pivoting in the closed direction (i.e., in the clockwise direction in FIG. 9). The ratchet groove 93 and the protrusion part 99 may alternatively be arranged on both of the pivoting faces 91b, but may be arranged only on one face as illustrated above.

The arms 94 and the lid 96 attached to the socket 91 are formed integrally with one another as a single piece. The arms 94 are provided as a pair corresponding to the axle pins 92, while being spaced from each other in the direction of the axle of pivoting. The arms 94 are formed like a plate which is flat in the direction of the axle of pivoting, and can pivot with the inner faces thereof slid over the pivoting faces 91b of the socket 91. In each arm 94, a hole 94a that engages with the axle pin 92 is formed. Each hole 94a possesses a polygonal shape conforming to the outer configuration of the axle pins 92. In the illustrated embodiment, one of the arms 94 has a clawed opening 97a in which the claw 97 is arranged. The claw 97 composes a non-return mechanism that engages with the teeth 93a of the ratchet groove 93 to allow pivoting from the open position to the closed position, while prohibiting the reverse pivoting.

The lid 96 is a plate-shaped member formed so as to lie across the pair of arms 94, with both side ends supported by the arms 94. Although not specifically limited, the lid 96 may alternatively be formed into a curved face as illustrated here. The lid 96 has at the center thereof a U-shaped cutout 96a. The cutout 96a is formed by cutting out a part of the lid 96, which comes near the axis of the needle hub 16 when the protector 90 is held in the open position as illustrated in FIG. 8. Provision of such cutout 96a produces a gap necessary for attaching the syringe 20, between the needle hub 16 and the lid 96. With the cutout 96a thus having the U shape which is oblong in the direction pivoting, the lid 96 can be pivoted to the closed position without interfering with the syringe 20, even when the syringe 20 is attached.

The socket 91 can be mounted on the protector 90 by aligning the legs 95 to the recesses 31a of the wide diameter part 30, and pressing them towards the wide diameter part 30. This allows the hooks 95a of the legs 95 to engage with the wide diameter part 30, to thereby fix the socket 91 on the wide diameter part 30. A molded article having the arms 94 and the lid 96 integrally molded therein is prepared, and the axle pins 92 are engaged with the holes 94a while keeping the arms 94 stretched apart, thus attaching the arms 94 and the lid 96 to the socket 91. The protector 90 is thus assembled to the needle hub 16.

The intradermal needle 10A of this embodiment is basically built as described above. Operations of these items will be explained below.

Figure 10:
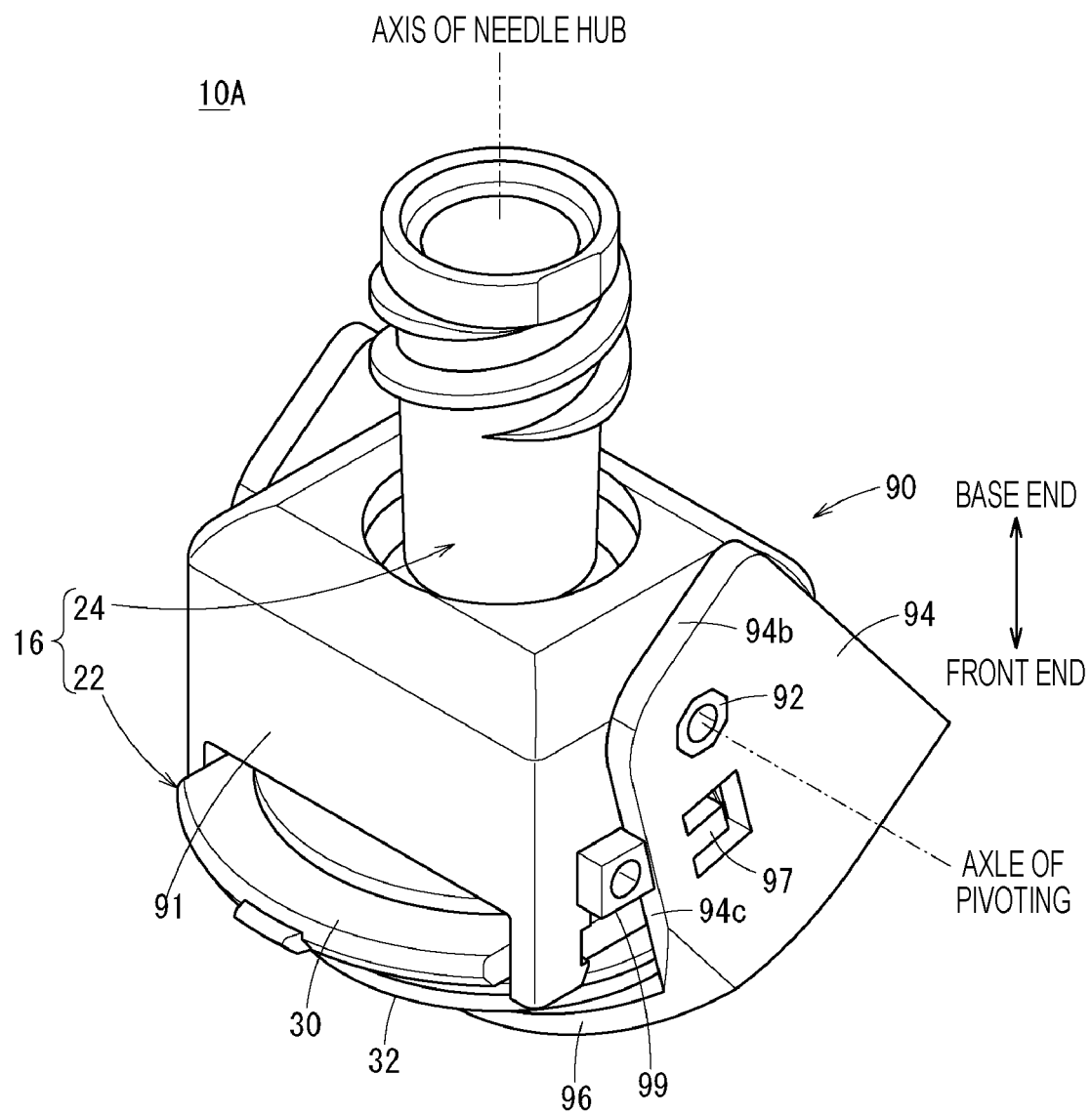
FIG. 10 is a perspective view illustrating the intradermal needle illustrated in FIG. 8, with the protector held in the closed position.

The intradermal needle 10A is marketed as a product while being enclosed in the packaged article 12A. The intradermal needle 10A is enclosed in the packaged article 12A with the protector 90 held in the open position, and becomes accessible to the user after the seal member 72 is peeled off from the container 70. The syringe 20 (see FIG. 4) is then assembled to the intradermal needle 10A. The protector 90 in this process is kept in the open position, with the aid of the resistive force in the direction of pivoting produced by the polygonal axle pins 92 (pivoting axle part) and the holes 94a. The protector 90 is kept in the open position also during use. After using the intradermal needle 10A, the user pivots the protector 90 with fingers to move the protector 90 to the closed position, as illustrated in FIG. 10.

The arms 94 of the protector 90 in this process pivot while keeping contact between the claw 97 of the arm 94 and the ratchet groove 93. The teeth 93a of the ratchet groove 93 have the upright faces on the side closer to the closed position, which allows pivoting towards the closed position only, while restricting pivoting towards the open position. The arms 94 stop pivoting upon contact with the protrusion part 99 in the closed position. Hence the arms 94 are restricted by the ratchet groove 93 and the claw 97, and thereby the protector 90 is kept locked in the closed position. That is, the protector 90 in the intradermal needle 10A is fixed in the closed position, since the ratchet groove 93 and the claw 97 act as a lock mechanism. The needle tip 14a is thus kept covered with the lid 96, making the intradermal needle 10A safely disposable.

In the aforementioned intradermal needle 10A, the axle pins 92 (pivoting axle part) are provided to the socket 91 mounted on the wide diameter part 30. This makes it possible to arrange the axle of pivoting of the axle pins 92 (pivoting axle part) on the base end side of the wide diameter part 30, so as to lie near the needle hub 16, with minimum working on the needle hub 16. In addition, since the protector 90 is designed to pivot centered round the axle of pivoting near the needle hub 16, so that the lid 96 of the protector 90 in the open position may be housed near the axis of the needle hub 16, thus improving convenience for housing of the intradermal needle 10A.

In the intradermal needle 10A, the pair of axle pins 92 are provided to a box-shaped socket 91, and the pair of arms 94 are provided corresponding to the individual axle pins 92. Since a part of the arm 94 near the axle of pivoting is supported by the box-shaped socket 91, so that the protector 90 will have further improved strength. Hence the protector 90 may be moved reliably to the closed position while preventing the arms 94 and the lid 96 from deforming, even under force applied from directions other than the direction of pivoting.

In the intradermal needle 10A, the wide diameter part 30 is provided with the cutout sides 31 that extend in the direction of pivoting of the arms 94, so that when the arms 94 is pivoted, the arms 94 are prevented from coming into contact with the wide diameter part 30. In addition, in the intradermal needle 10A, with the interval or distance between the pair of arms 94 being smaller than the diameter of the wide diameter part 30, the protector 90 may be downsized, thus improving convenience for housing in the packaged article 12A.

In the intradermal needle 10A, the polygonal shape of the axle pins 92 contributes to produce resistive force against pivoting of the protector 90. This successfully prevents the protector 90 from unintentionally pivoting to obstruct use of the intradermal needle 10A.

In the intradermal needle 10A, the ratchet groove 93 is provided to the socket 91, and the claw 97 that comes into contact with the ratchet groove 93 is provided to the arm 94. This successfully blocks the protector 90 from pivoting in the reverse direction, and prevents the needle tip 14a from being exposed, due to re-opening of the protector 90 having been held in the closed position.

The detailed description above describes embodiments of an intradermal needle, a packaged article that includes an intradermal needle, and an injection device representing examples of the inventive intradermal needle, packaged article and injection device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An intradermal needle comprising:
   a tubular needle having a needle tip configured to puncture a living body;
   a needle hub supporting the tubular needle and possessing a central axis extending through the needle hub;
   a flange fixed to and extending outwardly from the needle hub so that the flange is an enlarged diameter part of the needle hub;
   the needle hub including a first member that extends in a distal direction from the flange to a distal-most end of the needle hub, the needle hub also including a second member that extends in a proximal direction from the flange to a proximal-most end of the needle hub;
   the tubular needle projecting in the distal direction away from the needle hub;
   a pivotable protector that is pivotable about a pivot axis perpendicular to the central axis of the needle hub to pivot from an open position in which the needle tip is exposed and uncovered by the protector to a closed position in which the needle tip is covered by the protector;
   the protector being pivotably mounted on an axle part positioned proximal of the flange so that the protector pivots on the axle part about the pivot axis, the pivot axis being axially spaced from the flange in the proximal direction and passing through the second member;
   the pivot axis passing through the second member, the pivot axis passing through the axis of the needle hub or being adjacent the axis of the needle hub;
   the axle part being a first axle part and including a second axle part, the protector including two arms that each extend from a respective one of the first and second axle parts, and a lid supported by the arms, the needle hub being positioned between the two arms, and the lid being supported by the two arms, and
   a distance between the two arms is smaller than a diameter of the enlarged diameter part.

2. The intradermal needle according to claim 1, wherein the enlarged diameter part of the hub includes two sides positioned diametrically opposite from one another, the two sides each constituting a cutout side that is cutout from the enlarged diameter part, each of the cutout sides extending in a direction of pivoting of the arms.

3. The intradermal needle according to claim 1, further comprising a restriction member that restricts pivoting of the protector when the protector is in the open position and when the protector is in the closed position.

4. The intradermal needle according to claim 1, wherein the axle part is configured to produce a resistive force that resists pivoting of the protector.

5. The intradermal needle according to claim 1, further comprising a lock mechanism that fixes the protector in the closed position.

6. The intradermal needle according to claim 1, wherein the axle part is a first axle part and including a second axle part, the first and second axle parts projecting outwardly from the needle hub, the pivot axis passing through both the first and second axle parts, and the protector including two connection parts that each engage a respective one of the first and second axle parts.

7. The intradermal needle according to claim 6, wherein the first and second axle parts possess a non-circular outer shape and each of the connection parts engages the non-circular outer shape of the respective one of the first and second axle parts.

8. The intradermal needle according to claim 6, wherein the flange includes an outer dimension parallel to the pivot axis that is less than the outer dimension of the flange perpendicular to the pivot axis.

9. An intradermal needle comprising:
   a tubular having a needle tip configured to puncture a living body;
   a needle hub supporting the tubular needle and possessing a central axis extending through the needle hub;
   a flange fixed to and extending outwardly from the needle hub so that the flange is an enlarged diameter part of the needle hub;
   the needle hub including a first member that extends in a distal direction from the flange to a distal-most end of the needle hub, the needle hub also including a second member that extends in a proximal direction from the flange to a proximal-most end of the needle hub;
   the tubular needle projecting in the distal direction away from the needle hub;
   a pivotable protector that is pivotable about a pivot axis perpendicular to the central axis of the needle hub to pivot from an open position in which the needle tip is exposed and uncovered by the protector to a closed position in which the needle tip is covered by the protector;
   the protector being pivotably mounted on an axle part positioned proximal of the flange so that the protector pivots on the axle part about the pivot axis, the pivot axis being axially spaced from the flange in the proximal direction and passing through the second member; and
   a bracket mounted on and surrounding the second member of the needle hub, and the pivoting axle part being arranged on the bracket.

10. The intradermal needle according to claim 1, wherein the pivot axis passes through the second member, the pivot axis passing through the axis of the needle hub or being adjacent the axis of the needle hub.

11. The intradermal needle according to claim 10, wherein the axle part is a first axle part and including a second axle part, the protector including two arms that each extend from a respective one of the first and second axle parts, and a lid supported by the arms, the needle hub being positioned between the two arms, and the lid being supported by the two arms.

12. The intradermal needle according to claim 11, wherein a distance between the two arms is smaller than a diameter of the enlarged diameter part.

13. An intradermal needle comprising:
a tubular needle having a needle tip configured to puncture a living body;
a needle hub supporting the tubular needle and possessing a central axis extending through the needle hub;
a flange fixed to and extending outwardly from the needle hub so that the flange is an enlarged diameter part of the needle hub;
the needle hub including a first member that extends in a distal direction from the flange to a distal-most end of the needle hub, the needle hub also including a second member that extends in a proximal direction from the flange to a proximal-most end of the needle hub;
the tubular needle projecting in the distal direction away from the needle hub;
a pivotable protector that is pivotable about a pivot axis perpendicular to the central axis of the needle hub to pivot from an open position in which the needle tip is exposed and uncovered by the protector to a closed position in which the needle tip is covered by the protector;
the protector being pivotably mounted on an axle part positioned proximal of the flange so that the protector pivots on the axle part about the pivot axis, the pivot axis being axially spaced from the flange in the proximal direction and passing through the second member; and
a socket mounted on the needle hub and covering the enlarged diameter part, and the axle part being arranged on the socket.

14. The intradermal needle according to claim 13, wherein the socket has an outwardly facing sliding face over which the protector slides as the protector pivots from the open position to the closed position, and the sliding face includes a non-return mechanism that blocks reverse pivoting of the protector from the closed position towards the open position.

15. An intradermal needle comprising:
a tubular needle having a needle tip configured to puncture a living body;
a needle hub supporting the tubular needle and possessing a central axis extending through the needle hub;
a flange fixed to and extending outwardly from the needle hub so that the flange is an enlarged diameter part of the needle hub;
the needle hub including a first member that extends in a distal direction from the flange to a distal-most end of the needle hub, the needle hub also including a second member that extends in a proximal direction from the flange to a proximal-most end of the needle hub;
the tubular needle projecting in the distal direction away from the needle hub;
a pivotable protector that is pivotable about a pivot axis perpendicular to the central axis of the needle hub to pivot from an open position in which the needle tip is exposed and uncovered by the protector to a closed position in which the needle tip is covered by the protector;
the protector being pivotably mounted on an axle part positioned proximal of the flange so that the protector pivots on the axle part about the pivot axis, the pivot axis being axially spaced from the flange in the proximal direction and passing through the second member; and
the protector including a cutout part so that the protector encircles a portion of the needle hub.

16. A packaged article comprising:
an intradermal needle; and
a container in which is positioned the intradermal needle,
the intradermal needle including a tubular needle having a needle tip configured to puncture a living body; a needle hub supporting the tubular needle and possessing a central axis extending through the needle hub; a flange fixed to and extending outwardly from the needle hub so that the flange is an enlarged diameter part of the needle hub;
the needle hub including a first member that extends in a distal direction from the flange to a distal-most end of the needle hub, the needle hub also including a second member that extends in a proximal direction from the flange to a proximal-most end of the needle hub; and a pivotable protector that is pivotable about a pivot axis perpendicular to the central axis of the needle hub to pivot from an open position in which the needle tip is exposed and uncovered by the protector to a closed position in which the needle tip is covered by the protector, the protector being pivotably mounted on an axle part positioned proximal of the flange so that the protector pivots on the axle part about the pivot axis, the pivot axis being axially spaced from the flange in the proximal direction and passing through the second member; and
the container including a bottom face configured so that an inner diameter of the container is nearly equal to an outer diameter of the flange constituting the enlarged diameter part, the intradermal needle being positioned in the container with the protector in the open position.

17. The packaged article according to claim 16, wherein the axle part is a first axle part, and including a second axle part, the first and second axle parts projecting outwardly from the needle hub and being coaxial with one another, the pivot axis passing through both the first and second axle parts, and the protector including two connection parts that each engage one of the axle parts.

18. The packaged article according to claim 16, further comprising a projection that engages a groove to inhibit pivoting movement of the protector when the protector is in the closed position, the projection being provided on one of the needle hub and the protector while the groove is provided on the other of the needle hub and the protector.

19. The packaged article according to claim 16, wherein the second member of the needle hub includes an outwardly extending projection that is engageable with a syringe to connect the intradermal needle to the syringe, the outwardly extending projection on the second member being axially spaced from the axle part in the proximal direction so that the axle part is positioned axially between the flange and the outwardly extending projection.

20. The packaged article according to claim 19, wherein the outwardly extending projection is a screw thread.

21. An injection device comprising:
an intradermal needle; and
a syringe attached to the intradermal needle in a detachable manner,
the intradermal needle including a tubular needle having a needle tip configured to puncture a living body; a needle hub supporting the tubular needle and possessing a central axis extending through the needle hub; a flange fixed to and extending outwardly from the needle hub so that the flange is an enlarged diameter part of the needle hub; the needle hub including a first member that extends in a distal direction from the flange to a distal-most end of the needle hub, the needle hub also including a second member that extends in a proximal direction from the flange to a proximal-most end of the needle hub; a pivotable protector that is pivotable about a pivot axis perpendicular to the central axis of the needle hub to pivot from an open position in which the needle tip is exposed and uncovered by the protector to a closed position in which the needle tip is covered by the protector, the protector being pivotably mounted on an axle part positioned on the base end side of the flange so that the protector pivots on the axle part about the pivot axis, the pivot axis being axially spaced from the flange in the proximal direction and passing through the second member; and a protection that engages a groove to inhibit pivoting movement of the protector when the protector is in the closed position, the projection being provided on one of the needle hub and the protector while the groove is provided in the other of the needle hub and the protector.

22. The injection device according to claim 21, wherein the second member of the needle hub includes a screw thread that is engaged with a screw thread on the syringe, the screw thread on the second member being axially spaced from the axle part so that the axle part is positioned axially between the flange and the screw thread.

23. An intradermal needle comprising:
a tubular needle having a needle tip configured to puncture a living body;
a needle hub supporting the tubular needle and possessing a central axis extending through the needle hub;
a flange fixed to and extending outwardly from the needle hub so that the flange is an enlarged diameter part of the needle hub;
the needle hub including a first member that extends in a distal direction from the flange to a distal-most end of the needle hub, the needle hub also including a second member that extends in a proximal direction from the flange to a proximal-most end of the needle hub;
the tubular needle projecting in the distal direction away from the needle hub;
a pivotable protector that is pivotable about a pivot axis perpendicular to the central axis of the needle hub to pivot from an open position in which the needle tip is exposed and uncovered by the protector to a closed position in which the needle tip is covered by the protector;
the protector being pivotably mounted on an axle part positioned proximal of the flange so that the protector pivots on the axle part about the pivot axis, the pivot axis being axially spaced from the flange in the proximal direction and passing through the second member; and
the axle part being positioned on a bracket or socket that circumferentially surrounds an axially extending portion of the second member.

24. The intradermal needle according to claim 23, further comprising a projection that engages a groove to inhibit pivoting movement of the protector when the protector is in the closed position, the projection being provided on one of the needle hub and the protector while the groove is provided on the other of the needle hub and the protector.

* * * * *